United States Patent [19]

Mazur et al.

[11] Patent Number: 5,149,642

[45] Date of Patent: * Sep. 22, 1992

[54] PROCESS FOR PREPARING 2-ACYLGLYCERIDES OR 1,2 OR 2,3-DIACYLGLYCERIDES

[75] Inventors: Adam W. Mazur, Cincinnati; George D. Hiler, II; Magda El-Nokaly, both of Harrison, all of Ohio

[73] Assignee: The Procter & Gamble Company, Cincinnati, Ohio

[*] Notice: The portion of the term of this patent subsequent to May 26, 2009 has been disclaimed.

[21] Appl. No.: 511,674

[22] Filed: Apr. 20, 1990

[51] Int. Cl.$^5$ ............................ C12P 7/64; C12P 7/62; C12N 9/20
[52] U.S. Cl. .................................... 435/135; 435/134; 435/198
[58] Field of Search ................. 435/134, 135, 198

[56] References Cited

U.S. PATENT DOCUMENTS 4,865,978  9/1989  Serota .................................. 435/134

FOREIGN PATENT DOCUMENTS 64855    11/1982  European Pat. Off. .
237092    9/1987  European Pat. Off. .
0321777   6/1989  European Pat. Off. .
0234590  11/1985  Japan .
1-019042   1/1989  Japan .

OTHER PUBLICATIONS

El-Nokaly et al., ed., Microemulsions and Emulsions in Foods, Chapter 5, pp. 51-61, American Chemical Society, 1991.
Lazars et al., Proc.-World Conference on Emerging Technologies in the Fats and Oil Industry, "Synthesis of Esters by Liposes", pp. 346-354, 1986.
Grant and Hackh's, Chemical Dictionary, Fifth Edition, p. 40, 1987.
Meusel et al., Chemical Abstracts 109(12), Abstract No. 95091m, p. 102, 1988.

Primary Examiner—Douglas W. Robinson
Assistant Examiner—Mike Meller
Attorney, Agent, or Firm—Rose Ann Dabek; Jerry J. Yetter

[57] ABSTRACT

A process for the selective hydrolysis of triglycerides to mixtures of 1,3 or 2,3-diacyl glycerides and 2-acyl glycerides is disclosed. This process uses an alkyl alcohol selected from the group consisting of 2-methyl-2-propanol, 2-butanol and the primary, secondary or tertiary branched or straight chain alkyl alcohols having from 5 to 8 carbon atoms, and mixtures thereof, an aqueous buffer system and a 1,3-lipase. The 2-acyl glycerides in the mixture are esterified to make stereospecific 1,2-diacyl glycerides or 2,3-diacyl glycerides with acid anhydrides and a lipase catalyst. Under the reaction conditions, there is little rearrangement of the diacyl glycerides in the mixture and less than 20% triglyceride is formed. Stereospecific 1,2,4-triglycerides can be made from these materials by standard esterification reactions under conditions which control rearrangement.

17 Claims, No Drawings

PROCESS FOR PREPARING 2-ACYLGLYCERIDES OR 1,2 OR 2,3-DIACYLGLYCERIDES

FIELD OF THE INVENTION

This invention relates to a lipase-catalyzed regio- and stereoselective preparation of 1,2 or 2,3 diglycerides and the corresponding triglycerides. These triglycerides are prepared by regioselective hydrolysis of triglycerides to mixtures of 2-acyl glycerides and 2,3 or 1,2-diacyl glycerides followed by regio- and stereoselective acylation of the diglycerides to obtain specific triglyceride compounds.

BACKGROUND OF THE INVENTION

It has long been known that enzymic conversion of triglycerides to glycerol and fatty acids with 1,3-specific lipases, produces 1,2 or 2,3 diacyl glycerides and 2-monoglycerides as intermediates. However, only recently has this reaction been examined for practical preparation of stereospecific diglycerides. In general these reactions have been carried out by transesterification or hydrolysis in mechanically formed microemulsions using enzyme catalysis. Both methods require nearly anhydrous conditions.

The stereoselective acylation of regio and stereospecific diglycerides to form regiospecific triglycerides is also important. Cocoa butter substitutes, low calorie fats and other tailored triglycerides require such a synthesis.

BACKGROUND ART

European Patent Application 126,416 (Asahi Denka Kogyo, 1984) describes a continuous transesterification of fat or oil using lipase enzymes. The lipase has 1,3-specificity and is fixed on a porous solid or Chitosan derivative as a carrier. Preferably alcohols are added during the reaction. The most preferred alcohols are aliphatic alcohols having 4–18 carbons. The preferred are butyl, hexyl, octyl and decyl alcohols. The level of alcohol is 50–90 mol% of the free fatty acid estimated to be produced. The level of water is controlled so that 1,2-diglycerides are formed. Fatty acid is then added to make triglycerides. The water activity of the reaction mixture is from 0.5 to 0.9.

U.S. Pat. No. 4,865,978, issued to Serota (assigned U.S. Agricultural Department, 1989) describes the hydrolysis of triglycerides to fatty acid and glycerol with lipase through the formation of a "pseudo emulsion". The oil phase is divided into emulsion size particles suspended in the aqueous phase during mixing. These particles rapidly coalesce upon termination of the mixing. The reaction is carried out at temperatures of 20° C. to 45° C.

European Patent Application 64,855, issued to Halling et al. (assigned Unilever, 1982) discloses transesterification of fats by reaction in a water-immiscible organic liquid in contact with an enzyme in a water phase (containing no more than 4% water). Glycerides are transesterified with a lipase enzyme in the presence of fat, oil or fatty acid. The lipase is immobilized on a solid.

Japanese 62,061,591 (assigned Kao, 1985) describes an interesterification reaction using an enzyme in the presence of water, dihydric or trihydric alcohol (glycol or glycerol). The enzyme used is obtained by adding a water-insoluble carrier to a lipase containing medium which is then dried.

Japanese 61,173,791 (assigned Kao, 1986) describes the method for non-specific hydrolyzing oils using lipase in which the aqueous phase contained from 10% to 40% glycerine. After hydrolysis an oily layer, an emulsion and an aqueous layer are formed. The emulsion layer is recovered and reused.

Japanese 62,278,988 (assigned Kao, 1987) discloses an enzymic or microbial reaction. Two phases are prepared, a non-aqueous solution and an aqueous solution. The reaction occurs at the interface of these two phases.

European patent application 237,092, filed by Holmberg (assigned Berol Kemi, 1987) describes a transesterification of triglycerides which is carried out in the presence of a lipase with a hydrophobic part (organic solvent) and a surface active component in water under strictly controlled conditions. Hexane is used for the hydrophobic material. Both surfactants and auxillary surfactants are used. Alcohols and glycol ethers are listed as surface active components, including butanol, pentanol and hexanol.

In general, the described processes require low water activity or other strictly controlled conditions. No practical methods were available to control the ratio of 2-acylglyceride to 1,2-diglycerides over a broad range. Although methods involving microemulsions reportedly gave good yields of diglycerides, it was necessary to separate the diglyceride from the surfactant. This may not be easy due to the tendency of diacyl glycerides and monoacyl glycerides to rearrange when heated.

Accordingly, an economical process that would allow control of the ratio of diglcyeride to monoglyceride is desirable. The ability to produce high yields of 1,2 or 2,3-diacyl glycerides with little or no monoacyl glycerides or free glycerol is also highly desirable. It has been found that if the reaction is carried out in the presence of an alkyl alcohol selected from the group consisting of primary, secondary or tertiary pentanols hexanols, heptanols or octanols, including both the straight and branched chain isomers of these alcohols, and secondary and tertiary butanols and mixtures thereof, the reaction proceeds in high yield to a mixture of 2-acyl glyceride and 1,2 or 2,3 -diacyl glycerides. The triglyceride is suspended in a water immiscible solvent, for example, hexane, and the lipase is dissolved in an aqueous buffer. The alcohol is added to the reaction mixture. This reaction occurs without the presence of added emulsifiers or surfactants, and the lipase can be recovered and reused.

A clear advantage of this new process is the ability to control the course of hydrolysis by influencing the form of microstructures present in the reaction mixture. The hydrolysis generates products such as diglycerides, monoglycerides and acids known to undergo spontaneous formation of association structures, aggregates, microemulsions or liquid crystals if conditions permit. In particular, the presence of an alcohol modifies these microstructures, for example, it causes transition of liquid crystals to microemulsions. These phenomena can have a profound effect on a course of the hydrolysis reaction. Thus, the control of hydrolysis can be achieved by proper selection of solvents, the alkyl alcohols described herein, without addition of emulsifiers.

It is accordingly an object of this invention to produce mixtures of 1,2 or 2,3-diacyl glycerides and 2-acyl glycerides in specific ratios in yields of 80% or more. A ratio of from 80% diacyl glyceride to 20% monoglyceride to 20% acyl glyceride to 80% diacyl glyceride is achieved.

Another aspect of this invention is the regioselective enzymic acylation of 2-monoglycerides to regioselective 1,2-diglycerides or 2,3 diglycerides. These diglycerides can be esterified to produce triglycerides through the use of a normal esterification reaction using acid chlorides or acid anhydrides. This esterification can be carried out using enzymic or chemical catalysts.

All percentages herein are by weight unless otherwise indicated.

These and other objects of this invention will become obvious from the descriptions herein.

SUMMARY OF THE INVENTION

Described herein is a process for preparing 1,2 or 2,3-diacyl glycerides by enzymic hydrolysis comprising:

(1) mixing a water immiscible hydrocarbon, an alkyl alcohol selected from the group of branched chain, primary, secondary or tertiary alcohols having from five to eight carbons, and secondary and tertiary butanol and mixtures thereof, a triglyceride and an aqueous solution of a lipase enzyme having a pH of 4 to about 8 for from about 20° C. to about 50° C. for at least one hour; and separating the phases and optionally recovering the mixture of 2-acylglyceride and 1,2 or 2,3-diacylglyceride from the organic phase.

These mixtures can be esterified to make stereoselective diacyl glycerides. Stereospecific 1,2,3-triacyl glycerols can be prepared by reacting the 1,2-diglycerides or 2,3-diglyceride with an acid anhydride or an acid chloride under anhydrous conditions in the presence of a chemical catalyst, e.g., 4-N,N-dimethylaminopyridine or an enzymic catalyst.

DETAILED DESCRIPTION OF THE INVENTION

Triglycerides prepared according to this invention generally have the formula:

werein R stands for an alkyl saturated or unsaturated fatty acid acyl group. R, R' and R" can be equal to each other.

The alkyl fatty acids used herein preferably have from about to about 24 carbon atoms. Most preferably, the fatty acid in the 2 position has from 8 to 24 carbon atoms and fatty acids in the 1 and 3 positions, i.e. R and R", have from 8 to 24 carbon atoms. The fatty acids can be either saturated or unsaturated. The unsaturated fatty acids can be mono unsaturated fatty acids or polyunsaturated fatty acids. The position occupied by R and R" are the 1 and 3 positions, the position occupied by R' is the 2 position.

A. Definitions

By "2-acylmonoglyceride" or "2-acylglyceride" is meant a glycerol molecule esterified on the second carbon atom with a medium or long chain fatty acid.

By "1,2 or 2,3-diacyl glyceride" is meant a glycerol molecule esterified on the first and second carbon atoms (1,2) or on the third and second carbon atoms (2,3) with a medium or long chain fatty acid.

By "medium chain fatty acid," as used herein, is meant a saturated fatty acid, unsaturated fatty acid, or mixture thereof, having 6 to 10 carbon atoms.

By "medium chain fatty acid anhydride" as used herein, is meant the dehydration product of two medium chain fatty acids.

By "medium chain saturated fatty acid," as used herein, is meant $C_6$ (caproic), $C_8$ (caprylic), or $C_{10}$ (capric) saturated fatty acids, or mixtures thereof. The $C_7$ and $C_9$ saturated fatty acids are not commonly found, but they are not excluded from the possible medium chain fatty acids. The present medium chain fatty acids do not include lauric acid ($C_{12}$), sometimes referred to in the art as a medium chain fatty acid.

By "long chain fatty acid," as used herein, is meant a saturated fatty acid, unsaturated fatty acid, or mixture thereof, having 14 to 24 carbon atoms.

By "long chain saturated fatty acid," as used herein, is meant $C_{18}$ (stearic), $C_{19}$ (nonadecylic), $C_{20}$ (arachidic), $C_{21}$ (heneicosanoic), $C_{22}$ (behenic), $C_{23}$ (tricosanoic), or $C_{24}$ (lignoceric) saturated fatty acids, or mixtures thereof.

As used herein, the term "comprising" means various components or steps can be conjointly employed in the present invention Accordingly, the term "comprising" encompasses the more restrictive terms "consisting essentially of" and "consisting of."

All percentages, ratios and proportions used herein are by weight unless otherwise specified.

HYDROLYSIS OF TRIGLYCERIDES TO 2-MONOACYLGLYCERIDES

Hydrolysis of triglycerides to 1,2 or 2,3-diacyl diglycerides and 2-monoacyl glyceride is carried out in a two phase mixture of hydrocarbon and the starting triglycerides in a water immiscible phase and an aqueous phase comprising the buffer and a 1,3-specific lipase. The alkyl alcohol partitions between the aqueous phase and the organic phase.

The presence of alcohol has two functions. It inhibits hydrolysis of 2-acylglycerides to glycerol and it drives the reaction towards 1,2 or 2,3 diacyl glycerides and 2-monoglycerides. In its absence, the process reaches an early steady state characterized by high concentrations of triglycerides and diglycerides. Thus, extension of the reaction time in the absence of alcohols would not result in better yields of di- or monoglycerides but in the formation of glycerol. The higher branched chain secondary and tertiary alkyl alcohols, those having five to eight carbon atoms and 2-butanol and 2-methyl-2-butanol drive the reaction to form high levels of the regiospecific diacyl glycerides. Methanol and the primary butyl alcohols drive the reaction to form high yields of the 2-acyl glyceride. The propyl alcohols do not work in this reaction nor does ethanol. Mixtures of straight and branched alcohols having from five to eight carbons can also be used.

The primary hexanols are 1-hexanol, 2-methyl-1-pentanol, 4-methyl-1-pentanol, 3-methyl-1-pentanol, the secondary hexanols are 2-hexanol, 3-hexanol, 4-hexanol, 2-methyl-3-hexanol, 4-methyl-2-hexanol, The primary pentanols are 1-pentanol, 2-methyl-1-butanol, and 3-methyl-1-butanol. Secondary butanol is 2-butanol and t-butyl alcohol is 2-methyl-2-propanol.

The preferred alcohols for use herein are 2-butanol, t-butyl alcohol and 2,4-dimethyl-3-pentanol.

Any 1,3-specific lipase can be used for the hydrolysis. The lipases derived from the species aspergillus and rhizopus can be used. Specific lipases include aspergillus oryzae, aspergillus niger, mucor javanicus, mucor miehei, pancreatic, rhizopus delamar, rhizopus japonicus. These include MAP from Amano (Japan), lipolase and lipozyme from Novo (Netherlands). The amount of enzyme used is the amount of enzyme necessary to catalyze the reaction at a reasonable rate.

The enzyme concentration depends upon the amount of active protein in the enzyme preparation. Enzyme can be dried, immobilized on a resin or covvalently bonded to or absorbed on a support, or be in solution. The concentration needed to hydrolyze the triglyceride depends upon the form, the type and the activity of the enzyme. The amount required is a catalytic amount. A catalytic amount is enough to have the enzyme produce required 2-acyl glyceride and diglyceride mixtures at a reasonable rate but not so much as to force the reaction to form glycerine. One skilled in the art can easily determine the catalytic amount by running a small scale reaction and looking at the final products.

The triglyceride which has the requisite alkyl fatty acid in the 2, 1,2 or 2,3 position is dissolved in a hydrocarbon. The preferred hydrocarbons are the hexanes, petroleum ether, or isooctane. Any water immiscible hydrocarbon solvent which is essentially inert to the lipase can be used. Some solvents can denature enzymes. The solvent must dissolve the triglyceride at the temperature of the reaction. Since these triglycerides can be used in foods and pharmaceuticals, a food approved or edible hydrocarbon should be used. The hydrocarbon can be an alkane with from 5 to 10 carbons, an aromatic hydrocarbon such as benzene, toluene or xylene or halogenated hydrocarbons such as chloroform, methylene chloride or carbon tetrachloride. The preferred hydrocarbon solvents are hexane, pentane, petroleum ether and isooctane.

From about 3% to about 65% triglyceride is used in the reaction. Triglycerides which can be utilized in the hydrolysis reaction include triglycerides having $C_4$ to $C_{26}$ hydrocarbon chains with three fatty acid moieties. These materials can be derived from plants or animals or can be edible synthetic fats or oils. Liquid oils, e.g., unsaturated vegetable oils, can be used. Solid fats work only to the extent they are soluble in the solvent. These oils can be partially hydrogenated to convert some of the unsaturated double bonds of the fatty acid constituents into saturated bonds. Vegetable oils include soybean oil, hazelnut oil, linseed oil, olive oil, peanut oil, canola oil, safflower oil, rapeseed oil, cottonseed oil and sunflower seed oil can also be used herein.

Also suitable for use herein are the so-called low molecular weight synthetic fats which are certain tri- or diglycerides in which one or two of the hydroxyl groups of the glycerine have been esterified with acetic, propionic, butyric, hexanoic, capric or caprylic acids and one or two of the remaining hydroxyl groups of the glycerine have been esterified with a mixture of higher molecular weight fatty acids having from 8 to 22 carbon atoms. Especially preferred for use herein are symmetrical triglycerides as, e.g., tridecanoin or trioctanoin.

Other common types of triglycerides include: cocoa butter and cocoa butter substitutes, such as shea and illipe butter; milk fats, such as butter fat; and marine oils which can be converted into plastic or solid fats such as menhaden, pilcherd, sardine, whale and herring oils.

Preferred triglycerides are those derived from vegetable oils. These can be hydrogenated and unhydrogenated oils. Triglycerides of octanoic acid, decanoic acid and dodecanoic acid are preferred for use herein. Any unsaturated triglyceride containing unsaturated fatty acids is also preferred, e.g. triolein. The triglycerides of long chain fatty acids are usually not soluble in the hydrocarbon solvent or are solid at the reaction temperature. Therefore they are not preferred for use herein. Preferably the long chain fatty acids are used to esterify the 1,2-diglyceride to make the regiospecific triglycerides with a long chain acid.

The aqueous solution of the enzyme is buffered to a pH of about 4 to about 8. Standard buffer solutions which are not incompatible with the enzyme can be used. These include the phosphate buffers.

The reaction mixture has the following proportions by weight percent:

| | |
|---|---|
| 3% to 65% | triglyceride |
| 15% to 25% | aqueous buffer |
| 10% to 25% | alcohol |
| 0% to 60% | hydrocarbon |

The preferred ratio of alcohol to triglyceride is based on the amount of fatty acid generated by the hydrolysis. The alcohol serves several functions in this reaction. It reacts with the fatty acid to make an alkyl ester driving the reaction toward the 1,2 or 2,3 diacylglyceride, 2-acyl glyceride mixture; and it modifies any association structures present in the reaction mixture. When the alcohol is insoluble in water, it can be substituted for the hydrocarbon if the triglyceride is soluble in the alcohol.

The reaction is carried out at ambient temperature or at temperatures of from about 20° C. to about 50° C. for from 0.5 hours to about 8 hours. The reaction is mixed using a standard laboratory mixer.

The ratio of monoglyceride to diglyceride formed in this reaction is from 1:4 to 4:1.

The hydrocarbon layer is separated from the aqueous phase. A mixture of 1,2 or 2,3-diacyl glyceride and 2-monoglyceride are present in the hydrocarbon phase. Any conventional separation technique can be used to separage these materials if necessary.

For example, the 1,2 or 2,3-diacyl glyceride and 2-acyl glyceride mixture can be isolated from the organic phase by crystallization or evaporation of the organic solvent. Liquid 1,2 or 2,3-diacyl glycerides can be purified by distillation however, distillation frequently causes rearrangement or isomerization to the 1,3 diacyl glyceride.

The mixture can be esterified stereoselectively using acid anhydrides. It is not necessary to isolate the 2-acyl monoglyceride or the diglycerides from the organic phase if they are to be esterified. However, the solution should be dried to less than about 0.5% water to prevent hydrolysis of the acid anhydride. Any suitable drying agent such as magnesium sulfate, calcium chloride or other inert drying aid can be used. Excess anhydride could also be used, but this is less economical.

The excess primary alkyl alcohol should also be removed since it too can react with the acid anhydride to form the corresponding ester. On the other hand secondary and tertiary alcohols are usually not esterified in this reaction.

The monoglyceride and diglyceride mixture is reacted with an acid anhydride in an organic solvent. Any hydrocarbon, either alkyl or aromatic, or halogenated hydrocarbon can be used for this reaction. For example, petroleum ether, hexane, benzene, toluene, chloroform, methylene chloride and octane can be used.

A 1,3-specific lipase is added to the hydrocarbon mixture. The same lipases as were used to prepare the mixture of 2-acyl glyceride 1,2 or 2,3-diacyl glycerides by hydrolysis of triglycerides are suitable for this reaction. They include immobilized lipases and liposomes which are preferred. Catalytic amounts of lipase are used.

Any acid anhydride can be used to esterify the mixture of 2-acylglyceride and 1,2 or 2,3-diacyl glycerides. Acid anhydrides of alkyl fatty acids are commercially available or can be synthesized by conventional means.

The long chain fatty acids per se or naturally occurring fats and oils can serve as sources of the long chain saturated fatty acids. For example, soybean oil and high erucic acid rapeseed oil hydrogenated to an I.V. of about 10 or less are good sources of stearic and behenic fatty acids, respectively. Odd chain length long chain fatty acids can be derived from certain marine oils.

The esterification is conducted at temperatures of from about 20° C. to reflux temperature of the solvent (about 50° C.). Usually the esterification takes about 1 hour to about 5 hours.

The mole ratio of acid anhydride to 2-monoacyl glyceride glyceride is from about 1:1 to about 3:1 anhydride to monoglyceride. If necessary, the 1,2-diacyl glyceride or 2,3-diglyceride can be isolated by precipitation or crystallization. This reaction does not produce a high level of triglyceride, usually less than 20%.

The regiospecific 1,2-diacyl glycerides or 2,3 diacyl glycerides can be converted to stereospecific triglycerides by any conventional esterification reaction. Such techniques include esterification with acid chlorides or acid anhydrides under essentially anhydrous conditions (0.5% or less water). Other catalytic reactions which are known not to cause rearrangement can be used. For example esterification with a fatty acid in the presence of 0.3% to about 1% (mole weight basis) of 4,-N,N-dimethyl-aminopyridine can be used to make stereospecific triglycerides from 1,2-diacylglycerides. Catalysts which are known to induce rearrangement should be avoided as they will cause the 1,2-diacyl glyceride, 2,3-diacyl glyceride or the resultant triglyceride to rearrange, thus producing a mixture of materials and not the regiospecific triglycerides that are desired.

The purified mixture of stereospecific triglycerides can also be subjected to bleaching and deodorizing steps for color and flavor/aroma improvement using conventional techniques well known in the fats and oils art. Alternatively, the reaction mixture can be bleached using conventional bleaching earth and/or activated carbon prior to purification. In the case of stereospecific triglycerides which have unsaturated fatty acid residues or mixtures of unsaturated and saturated fatty acid residues, the stereospecific triglycerides can be hydrogenated, before or after purification, to convert the unsaturated fatty acid residues to saturated fatty acid residues.

Uses of Stereospecific Triglycerides as Reduced Calorie Fats

Stereospecific triglycerides of the type MML/MLM obtained according to the present invention (where L is a long chain saturated fatty acid residue and M is a medium chain saturated fatty acid residue) can be used as reduced calorie fats to partially or totally replace normal triglyceride fat in any fat-containing food composition comprising fat and nonfat ingredients to provide reduced calorie benefits. In order to obtain a significant reduction in calories, it is necessary that at least about 50% of the total fat in the food composition, or at least about 20% of the caloric value of the food, comprise the reduced calorie fat.

EXAMPLE I

Trioctanoin (67.6 mmole, 31.79 g) is dissolved in hexane (60 ml) and 2-butanol (20 ml). This solution is mixed with 50mM phosphate buffer (20 ml) containing lipolase 100L (Novo) (0.3 g) and stirred at 20° C. for 4 hours. The organic phase containing approximately 48 mol % of 2-octanoyl glycerol, 45% mol % of 1,2(2,3)-dioctanoyl glycerol and 7 mol % of unreacted trioctanoin is separated and dried with anhydrous magnesium sulfate for 15 minutes. This mixture is treated with decanoic anhydride (0.2 mol, 65 g), lipozyme (Novo) (7 g) and methylene chloride (100 ml). After 90 min., the reaction produced a mixture containing approximately 85 mol % of 1,2(2,3)-diglycerides, 12 mol % of triglycerides and 3 mol % of unreacted 2-monoglycerides. Further addition of behenic anhydride (60 mmole, 40 g) and 4-N,N-dimethylaminopyridine (8 mmole, 1g) gives 85 mol % of 1-behenyl triglycerides, 3 mol % of 1,2-dibehenyl triglycerides and 12 mol % of the remaining medium chain triglycerides. This mixture is conveniently separated by means of molecular distillation to give pure 1-behenyl triglycerides.

EXAMPLE II

1-Docosanoyl-2-decanoyl-3-octanoyl rac-glycerol.

A solution of 1-docosanoyl-2-decanoyl glycerol (24.6 mmole, 14.0 g), decanoic anhydride (26.8 mmole, 7.25 g) and 4-N,N-dimethylaminopyridine (DMAP) (1.25 mmole, 0.15 g) in methylene chloride (500 ml) is stirred at room temperature for 4 hours. Solvent is evaporated, the oily residue is dissolved in petroleum ether (500 ml) and cooled in dry ice. The precipitated product is filtered and dried under vacuum. Yield of 1-docosanoyl-2-decanoyl-3-octanoyl rac-glycerol is 13.8 g (81%).

EXAMPLE III

1-Docosanoyl-2-octanoyl-3-decanoyl rac-glycerol is prepared from 1-docosanoyl-2-octanoyl rac-glycerol (18.5 mmole, 10.0 g) and decanoic anhydride (18.5 mmole, 6.05 g) with DMAP (0.5 g) analogously to Example V with the yield 11 g (85%).

EXAMPLE IV

1-Decanoyl-2-docosanoyl-3-octanoyl rac-glycerol is prepared from 1-decanoyl-2-docosanoyl rac-glycerol (7.9 mmole, 4.5 g) and octanoic anhydride (7.9 mmole, 2.14 g) analogously to Example V with the yield 4.1 g (75).

What is claimed is:

1. A process for preparing mixtures of 2-acyl glycerides and 1,2 or 2,3-diacyl glycerides comprising:
   (A) mixing for at least one hour at a temperature of from 20° C. to 50° C.
      (1) from 15% to 25% aqueous buffer containing a catalytic amount of 1,3-specific lipase enzyme, said aqueous buffer, having a pH from about 4 to about 8;
      (2) from 20% to 60% water immiscible hydrocarbon;

(3) from 3% to 65% triglyceride; and
(4) from 10% to 25% of an alkyl alcohol selected from the group consisting of secondary butanols; tertiary butanols; primary, secondary and tertiary alkyl alcohols having from 5 to 8 carbon atoms; and mixtures thereof; and (B) separating the water immiscible hydrocarbon layer containing the 2-acyl glyceride and 1,2 or 2,3-diacyl glycerides.

2. A process for preparing stereoselective diglycerides comprising the steps of:
(1) forming a mixture of 1,2-or 2,3 diacyl glyceride and 2-acyl glyceride by;
  (A) mixing for at least one hour at a temperature of from 20° C. to 50° C.
    (i) from 15% to 25% aqueous buffer containing a catalytic amount of 1,3-specific lipase enzyme, said aqueous buffer, having a pH from about 4 to about 8;
    (ii) from 20% to 60% water immiscible hydrocarbon;
    (iii) from 3% to 65% triglyceride; and
    (iv) from 10% to 25% of an alkyl alcohol selected from the group consisting of secondary butanols; tertiary butanols; primary, secondary and tertiary alkyl alcohols having from 5 to 8 carbon atoms; and mixtures thereof; and
  (B) separating the water immiscible hydrocarbon layer containing the 2-acyl glyceride and 1,2 or 2,3-diacyl glycerides;
(2) reacting said mixture with an acid anhydride, a catalytic amount immobilized lipase in a water immiscible solvent for from 0.5 hours to 5 hours at a temperature of from 20° C. to 50° C. to form stereoselective 1,2-diacyl or 2,3-diacyl glycerides.

3. A process according to claim 1 wherein said enzyme is a solid or in solution.

4. A process according to claim 3 wherein said hydrocarbon is selected from the group of consisting of alkyl hydrocarbons having from 5 to 10 carbons.

5. A process according to claim 4 wherein said triglyceride is selected from the group consisting of fatty acid triglycerides wherein said fatty acids have from 8 to 24 carbon atoms.

6. A process according to claim 5 wherein said triglyceride is selected from the group consisting of partially hydrogenated or unhydrogenated sunflower seed oil, soybean oil, canola, rapeseed oil, safflower oil, marine oils, corn oil and mixtures thereof.

7. A process according to claim 5 wherein said triglyceride contains octanoic acid or decanoic acid in the 2 or 3 position.

8. A process according to claim 2 wherein said alcohol is selected from the group consisting of 2-butanol, 2-methyl-2-butanol, and 2,4-dimethyl-3-pentanol.

9. A process according to claim 8 wherein said enzyme is a solid or in solution.

10. A process according to claim 9 wherein said hydrocarbon is selected from the group of consisting of hexane, pentane, isooctane, petroleum ether and mixtures thereof.

11. A process according to claim 10 wherein said triglyceride is selected from the group consisting of fatty acid triglycerides wherein said fatty acids are saturated or unsaturated fatty acids having from 8 to 24 carbon atoms.

12. A process according to claim 11 wherein said triglyceride is selected from the group consisting of partially hydrogenated or unhydrogenated sunflower seed oil, soybean oil, canola, rapeseed oil, safflower oil, marine oils, corn oil and mixtures thereof.

13. A process according to claim 12 wherein said triglyceride contains octanoic acid or decanoic acid in the 2-position.

14. A process according to claim 13 wherein said water-immiscible hydrocarbon in step 2 is selected from the group consisting of benzene, toluene, hexane, petroleum ether, methylene chloride, and chloroform and mixtures thereof.

15. A process according to claim 2 wherein the regiospecific 1,2 or 2,3-diacylglycerides are esterified with a fatty acid anhydride in the presence of N,N-dimethylaminopyridine.

16. A process according to claim 15 wherein said fatty acid anhydride is behenic acid.

17. A process according to claim 2 wherein said mixture of 2-acyl glyceride and 1,2 or 2,3-diacyl glycerides are isolated from the water immiscible hydrocarbon layer before the reaction with the acid anhydride in step (2).

* * * * *